United States Patent [19]
Gulsby

[11] Patent Number: 5,662,641
[45] Date of Patent: Sep. 2, 1997

[54] DISPOSABLE DIAPER WITH FLAP FOR CONCEALING TAPE TABS

[76] Inventor: Lanoma Gulsby, 2364 Cattleman Rd., Sarasota, Fla. 34232

[21] Appl. No.: 589,354

[22] Filed: Jan. 19, 1996

[51] Int. Cl.$^6$ .................... A61F 13/15; A61F 13/20
[52] U.S. Cl. .................... 604/385.1; 604/386; 604/389
[58] Field of Search .................... 604/385.1, 386, 604/387, 381, 390, 391, 392

[56] References Cited

U.S. PATENT DOCUMENTS

| | | | |
|---|---|---|---|
| 3,089,494 | 5/1963 | Schwartz | 604/389 |
| 3,882,871 | 5/1975 | Taniguchi | 604/391 |
| 4,051,854 | 10/1977 | Aaron | 604/394 |
| 4,834,742 | 5/1989 | Wilson et al. | 604/389 |
| 4,988,346 | 1/1991 | Pfefferkorn | 604/389 |
| 5,342,685 | 8/1994 | Gobran | 604/389 |
| 5,368,585 | 11/1994 | Dokken | 604/385.1 |

FOREIGN PATENT DOCUMENTS 0532034  3/1993  European Pat. Off. .

*Primary Examiner*—Mark O. Polutta
*Attorney, Agent, or Firm*—Charles J. Prescott

[57] ABSTRACT

An absorbent, disposable diaper for a baby which may not be inadvertently removed by the baby. The invention is thus directed to a diaper having an additional flap connected along one preferably lower margin thereof to a front panel or second waistband portion of the diaper for covering or concealing the distal ends of each of a pair of tabs which extend from the corners of a back panel or first waistband portion of the diaper for adhesive attachment onto the outer surface of the second waistband portion.

3 Claims, 3 Drawing Sheets

DISPOSABLE DIAPER WITH FLAP FOR CONCEALING TAPE TABS

BACKGROUND OF THE INVENTION

1. Scope of Invention

This invention relates generally to disposable absorbent diapers and more particularly to a disposable diaper adapted to be secured in place by adhesive tabs and having means for preventing inadvertent tab detachment by a baby wearing the diaper.

2. Prior Art

Absorbent disposable diapers have virturally replaced all reusable, washable diapers by providing substantial advantage, convenience and absorbency. These disposable diapers comprise a generally quadrilateral absorbent panel having various arrangements of absorbent and water resistant layers combined therein. Additionally, most such disposable diapers further include adhesive tabs connected to the back panel thereof for releasible attachment onto the front panel of the diaper after being securely wrapped and drawn around the waist of the baby.

The following U.S. patents represent applicant's awareness of prior patented disposable diaper products and associated attachment means therefor;

| | |
|---|---|
| 5,370,639 | Widlund |
| 3,921,639 | Cepuritis |
| 3,930,502 | Tritsch |
| 5,176,670 | Roessier, et al. |
| 4,493,713 | Izzo |
| 4,769,024 | Pike, et al. |
| 4,378,800 | Schaar |
| 4,968,311 | Chickering, et al. |
| 3,920,019 | Schaar |
| 3,901,239 | Tritsch |

Because it is most convenient for positioning the disposable diaper around the baby with the baby laying on its back, the adhesive tabs are most effectively connected to and laterally extending from each corner of the back panel. Thus, when drawn forwardly in overlapping fashion around the front panel, the diaper is easily secured in position.

An unanticipated problem has developed with respect to these disposable absorbent diapers which have these releasibly attachable adhesive tabs for attachment. In most instances, these tape tabs as discussed above are adhered directly against the front panel or a plastic cover sheet which covers a portion of the outer surface of the front panel for releasibly reattachment of the adhesive tabs. The distal ends of these attached tape tabs are easily accessible to the baby's hands and are easily rubbed, grabbed or otherwise dislodged during active hand movement and grasping of the baby. Of course, the consequences are usually very unpleasant to deal with and, at best, the parent or caretaker observes the inadvertent releasing of these tape tabs and immediately deals with the problem. Discovery at a later time would, of course, present further complications to this problem.

One prior U.S. patent known to applicant, U.S. Pat. No. 5,133,706, invented by Dixon teaches a disposable diaper provided with an adhesive tab construction having one end secured thereto, the other free end having a detachable portion defined by perforations to effect its removal after attachment of the tab.

The present invention provides an additional protective flap attached at one end to a front panel of the disposable diaper and releasibly attachable at another opposite edge portion thereof to the front panel whereby the opposing ends of each tape tab attached to the front panel of the diaper are covered or concealed so as to prevent inadvertent grabbing and rubbing of either of the tape tabs which could otherwise lead to inadvertent dislodgement or detachment.

BRIEF SUMMARY OF THE INVENTION

This invention is directed to an absorbent, disposable diaper for a baby which may not be inadvertently removed by the baby. The invention is thus directed to a diaper having an additional flap connected along one preferably lower margin thereof to a front panel or second waistband portion of the diaper for covering or concealing the distal ends of each of a pair of tabs which extend from the corners of a back panel or first waistband portion of the diaper for adhesive attachment onto the outer surface of the front panel or second waistband portion.

It is therefore an object of this invention to provide an improved disposable absorbent baby diaper which prevents inadvertent rubbing and dislodgement of its adhesive attaching tabs.

It is yet another object of this invention to provide a disposable absorbent baby diaper which resists baby's hand rubbing and grasping of the ends of the tape tabs after being installed.

It is still another object of this invention to prevent the inadvertent removal of a soiled baby diaper prior to a desired changing thereof.

In accordance with these and other objects which will become apparent hereinafter, the instant invention will now be described with reference to the accompanying drawings.

DETAILED DESCRIPTION OF THE INVENTION

Figure 1:
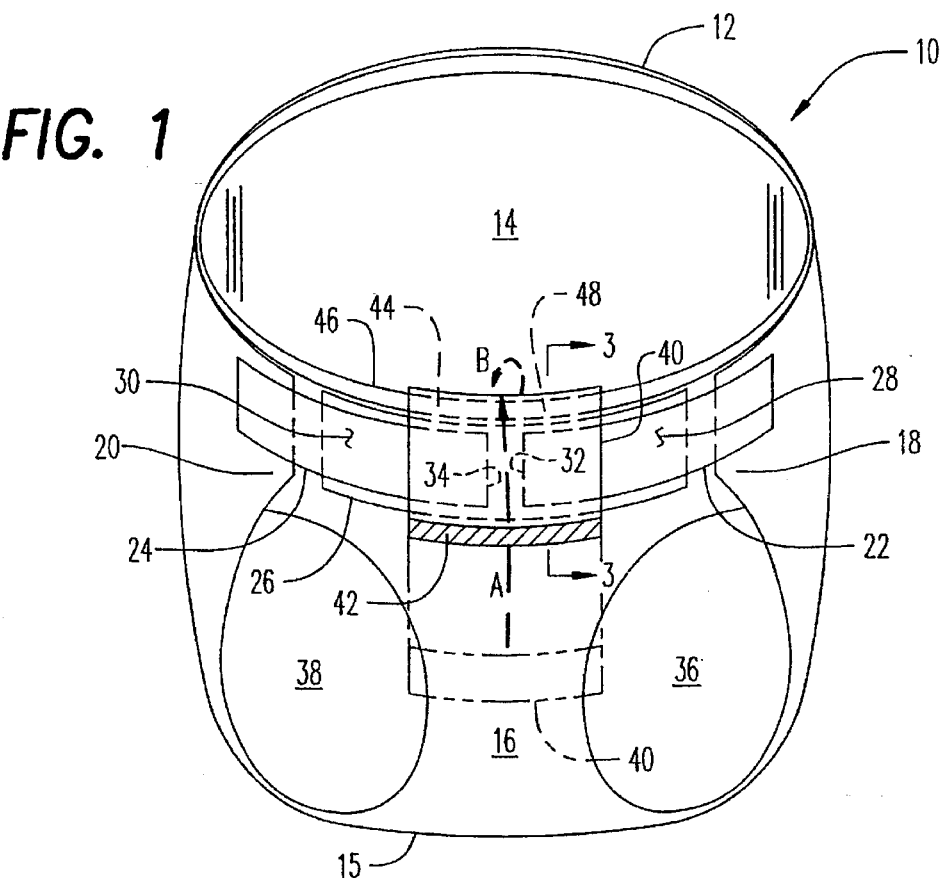
FIG. 1 is a perspective view of one embodiment of the invention in an in-use configuration.
Figure 3:
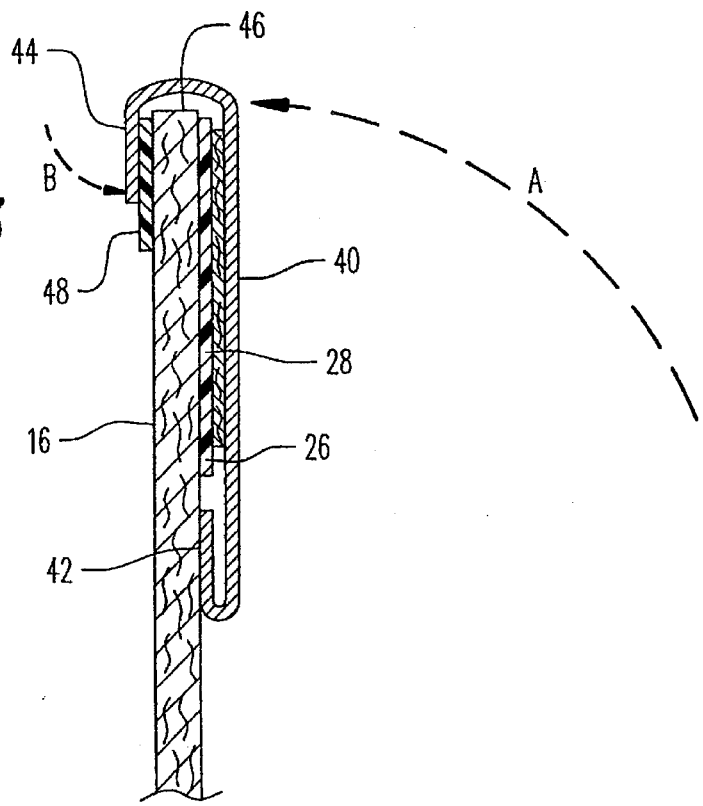
FIG. 3 is a section view in the direction of arrows 3—3 in FIG. 1.

Referring now to the drawings, and particularly to FIGS. 1 and 3, one embodiment of the invention is there shown generally at numeral 10. This disposable diaper 10 includes a generally rectangular absorbent member 12 having a first waistband portion or back panel 14 and a second waistband portion or front panel 16 extending in either direction from an intermediate or bottom portion 15 of the disposable diaper 10.

A pair of tape tabs 28 and 30 are attached and laterally extend from each corner 18 and 20 of the first waistband portion 14. These tape tabs 28 and 30 include an adhesive inwardly facing surface which is typically protected prior to use by a thin, removable cover sheet (not shown).

The second waistband portion 16 having a front margin 46 typically includes a plastic adhering sheet 26 securely, permanently attached to the outer upper surface thereof which provides an attaching surface for the adhesive coated tape tabs 28 and 30 as shown. When in position around the baby, with the legs of the baby passing through openings 36 and 38 in a conventional manner, the distal or free ends 32 and 34 of each tape tab 28 and 30, respectively, generally oppose one another and are spaced slightly apart as shown. It is primarily these distal ends 32 and 34 upon which the baby's hands are easily inadvertently rubbed, leading to tab disengagement and one big mess.

Figure 4:
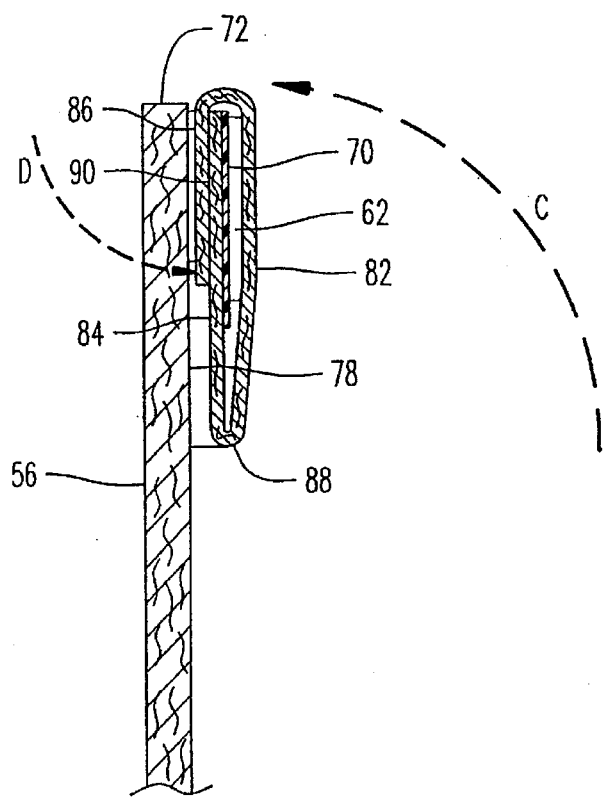
FIG. 4 is a section view in the direction of arrows 4—4 in FIG. 2.

A flexible flap 40 formed of disposable sheet material of a convenient composition is attached to the outer surface of the second waistband portion 16 at region 42 by either permanent adhesive, heat sealing and the like. The flap 40 is shown in phantom in its free orientation and in solid line in its secured in-use position by, as best seen in FIG. 4, first pivoting the flap 40 in the direction of arrow A after the tape tabs 28 and 30 have been secured in position as shown. The upper portion 44 of flap 40 is then further pivoted in the direction of arrow B in FIG. 3 to be adhesively secured against a second plastic strip 48 permanently attached onto the inner surface of second waistband portion 16. By the arrangement shown in FIGS. 1 and 2, it should be evident that the addition of flap 40, when in its in-use position shown in solid lines, prevents the inadvertent rubbing or grasping and detachment of both of the tape tabs 28 and 30. Moreover, the flap 40 is easily disengaged by reversing the attaching procedure by first detaching flap portion 44 in the opposite direction from arrow B and then pivoting the flap 40 itself away from covering engagement opposite from the direction of arrow A.

Figure 2:
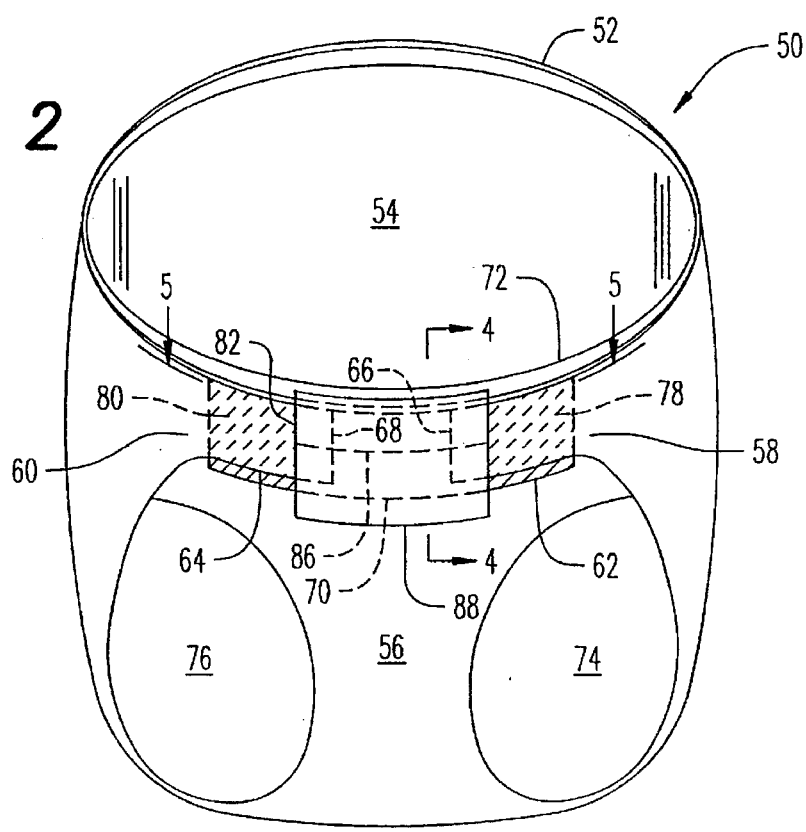
FIG. 2 is a perspective view of another embodiment of the invention in an in-use configuration.
Figure 5:
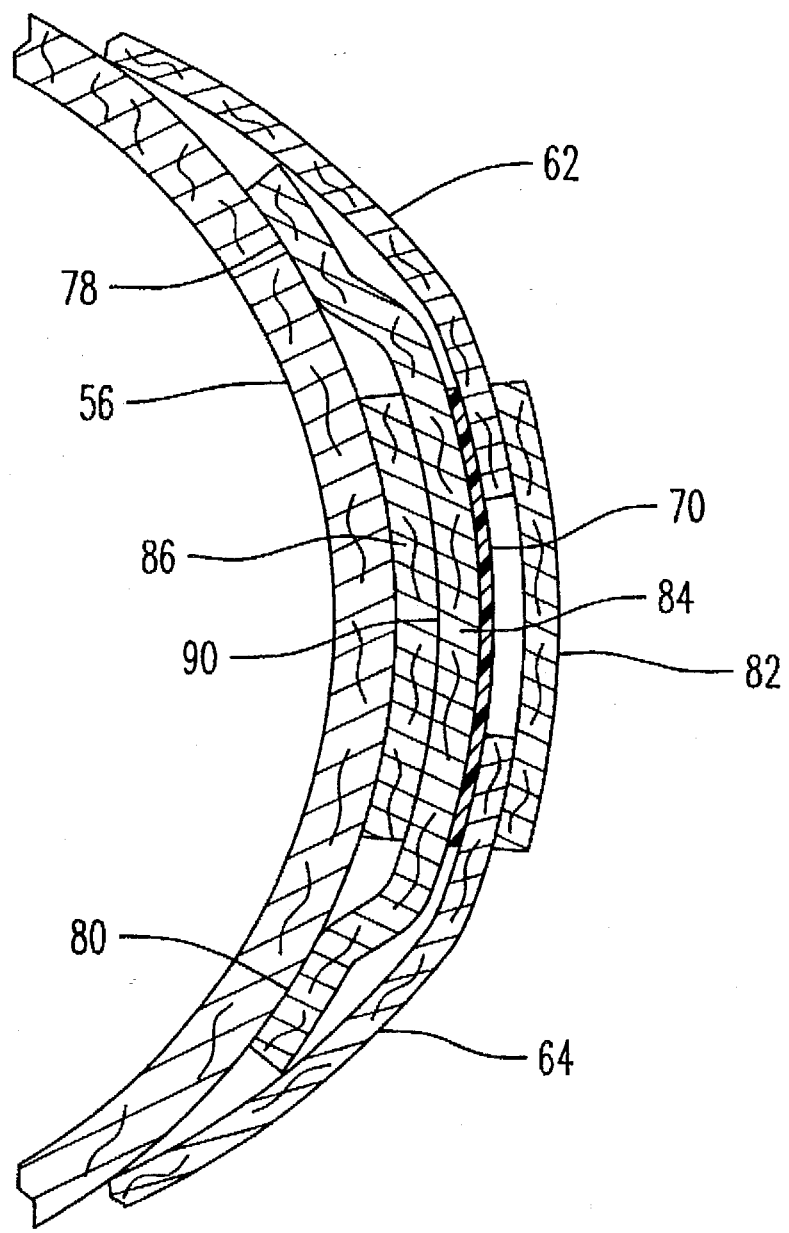
FIG. 5 is a section view in the direction of arrows 5—5 in FIG. 2.

Referring now to FIGS. 2, 4, and 5, another embodiment of the invention is there shown at numeral 50 in an in-use configuration absent the torso of the baby. This embodiment 50 also includes a conventional disposable absorbent generally rectangular sheet 52 having a back panel or first waistband portion 54 and a front panel or second waistband portion 56 which, when formed around the baby in the configuration shown, define leg openings 74 and 76.

This embodiment 50 also includes tape tabs 62 and 64 which laterally extend from each corner 58 and 60 of the first waistband potion 54.

As in the previous embodiment 10, this embodiment 50, when installed, disposes the end margins 66 and 68 of the tape tabs 62 and 64, respectively in a spaced and opposing relationship one to another as shown. This embodiment 50 also includes a flap 82 formed of flexible disposable sheet material as desired and is attached at spaced apart regions 78 and 80 to the front outer surface of the second waistband potion 56 as shown in FIG. 2. These tape tabs 62 and 64 have an inner adhesive surface which adhesively attaches to a plastic sheet 70 permanently attached just below the waistband margin 72 of the outer surface of the second waistband portion 56. After each of the tape tabs 62 and 64 are secured to the plastic sheet 70, the flap 82 is first pivoted about lower fold margin 88 in the direction of arrow C in FIG. 4, after which edge potion 86 is tucked into the position shown between the flap potion 84 and the outer surface of the second waistband portion 56. To prevent inadvertent dislodgement of the flap potion 86, an adhesive interface at 90 is also provided between these mating surfaces of the flap 82 itself.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. An absorbent disposable baby diaper comprising:

a sheet of absorbent, flexible, disposable material defining front, back and intermediate portions;

first and second waistband portions disposed at an end of said front and back portions, said first and second waistband portions adapted to overlap each other when encircling a waist of a baby;

tab means disposed at each end of said first waistband portion for releasibly connecting said first and second waistband portions to one another in overlapping fashion around the waist;

flap means formed of flexible, disposable sheet material for covering at least each distal end portion of each said tab means, and including means for concealing a distal margin of said flap means whereby the baby may not inadvertently detach either of said tab portions or said flap means.

2. A disposable absorbent diaper securable about a body of a baby, comprising:

a generally rectangular sheet of absorbent, flexible, disposable material defining front and back panels and an intermediate portion thereof;

said back panel defining a first end of said diaper and having a pair of tape tabs at said first end of the diaper, each tape tab having an adhesive surface and being positioned in close proximity to, and extending laterally from each corner of said first end of said diaper;

a tape receiving surface means on said front panel for releasibly fastening said pair of tape tabs thereagainst;

flap means formed of flexible, disposable sheet material attached to said front panel for covering said tape tabs portions and including means for concealing a distal margin of said flap means whereby the baby may not inadvertently detach either of said tape tabs or said flap means.

3. A disposable absorbent diaper which can be secured about a body of a baby comprising:

a generally rectangular sheet of absorbent, flexible, disposable material defining front and rear panels and an intermediate portion thereof;

said rear panel having corners and said front panel positionable on the baby opposite said rear panel;

a pair of adhesive coated tape tabs each being positioned in close proximity to a respective one corner of said rear panel, each said tape tab being a lateral extension of said rear panel;

a plastic strip attached on an outer surface of said front panel;

said plastic strip having an exposed plastic surface away from the baby serving as a tape-receiving surface for releasibly fastening said pair of tape tabs thereagainst when putting said diaper on the baby;

a flap formed of flexible, disposable sheet material connected along a lower margin thereof to said front panel upwardly extending to cover at least a portion of each said tape tab, an upper margin of said flap which extends beyond said tape tabs releasibly attachable to an inner surface of said front panel whereby the baby may not inadvertently disengage either of said tab portions or said flap.

* * * * *

UNITED STATES PATENT AND TRADEMARK OFFICE
CERTIFICATE OF CORRECTION

PATENT NO. : 5,662,641
DATED : September 2, 1997
INVENTOR(S) : Lanoma Gulsby

It is certified that error appears in the above-indentified patent and that said Letters Patent is hereby corrected as shown below:

Column 4, line 45, replace "comers" with -- corners --.

Signed and Sealed this

Sixth Day of January, 1998

Attest:

BRUCE LEHMAN

*Attesting Officer*      *Commissioner of Patents and Trademarks*